United States Patent [19]

Henrick

[11] 4,229,352

[45] Oct. 21, 1980

[54] BENZYLPYRROLYLMETHYL ESTERS OF CYCLOPROPANE CARBOXYLIC ACIDS

[75] Inventor: Clive A. Henrick, Palo Alto, Calif.

[73] Assignee: Zoecon Corporation, Palo Alto, Calif.

[21] Appl. No.: 66,263

[22] Filed: Aug. 13, 1979

Related U.S. Application Data

[63] Continuation-in-part of Ser. No. 942,509, Sep. 15, 1978.

[51] Int. Cl.$^3$ .............................................. C07D 207/32
[52] U.S. Cl. ................................. 260/326.43; 424/274
[58] Field of Search ..................................... 260/326.43

[56] References Cited

U.S. PATENT DOCUMENTS 4,056,628  11/1977  Winternitz ........................... 424/308

FOREIGN PATENT DOCUMENTS 2843760  4/1979  Fed. Rep. of Germany .

*Primary Examiner*—Dolph H. Torrence

[57] ABSTRACT

Benzylpyrrolylmethyl esters of ether and thioether substituted cyclopropanecarboxylic acids, synthesis thereof, and intermediates therefor, such esters being useful as pesticides.

17 Claims, No Drawings

BENZYLPYRROLYLMETHYL ESTERS OF CYCLOPROPANE CARBOXYLIC ACIDS

This is a continuation-in-part of Ser. No. 942,509, filed Sept. 15, 1978, the entire disclosure of which is incorporated herein by reference.

This invention relates to novel esters of substituted cyclopropane carboxylic acid, synthesis thereof and intermediates therefor, such esters being useful as pesticides.

The novel compounds of the present invention are represented by the following generic formula (A):

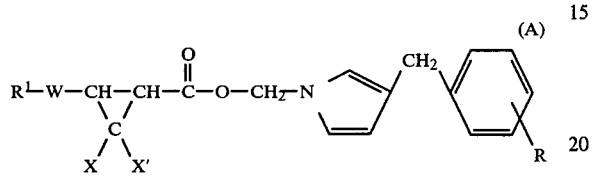

wherein,
W is oxygen or sulfur;
X is lower alkyl or halogen;
X' is hydrogen, lower alkyl or halogen;
R$^1$ is lower alkyl, lower haloalkyl, lower alkenyl, lower haloalkenyl, or the group

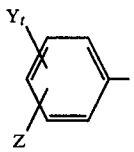

in which
t is zero, one, two, three or four;
Y is independently selected from hydrogen, lower alkyl, lower haloalkyl, lower alkoxy, lower alkylthio, lower alkylcarbonyl, lower alkoxycarbonyl, lower acyloxy, halogen, cyano, nitro and lower haloalkylthio;
Z is independently selected from the values of Y, cycloalkyl and lower haloalkoxy; or together with Y forms a methylenedioxy group; and
R is hydrogen, fluoro, bromo, chloro, trifluoromethyl, methyl, methoxy or methylthio.

The compounds of the present invention represented by generic formula (A) are useful agents for the control of pests such as insects and acarids. Without any intention of being bound by theory and although the mode of action of the compounds of formula (A) as applied to the control of insects and acarids is not completely understood, the compounds of formula (A) appear to be effective for the control of insects and acarids by reason of mechanisms of the nature of the insect control agents known as pyrethrins and synthetic pyrethroids.

In the description hereinafter and the appended claims, each of R, R$^1$, W, X, X', Y, Z and t is as defined hereinabove, unless otherwise specified.

The compounds of formula (A) can be prepared by the reaction of an acid of formula I or the acid halide thereof with an alcohol of formula IA. For example, the acid I is reacted with thionyl chloride in the presence of a solvent such as hexamethylphosphoric triamide (HMPT), dimethylformamide (DMF), tetrahydrofuran (THF) and the like, and then with the alcohol in the presence of a catalyst such as 4-dimethylaminopyridine.

Alternatively, an acid of formula I is reacted with the halide, e.g., bromide, or mesylate corresponding to the alcohol IA in the presence of a base such as potassium carbonate and the like in an organic solvent to prepare the esters of formula (A).

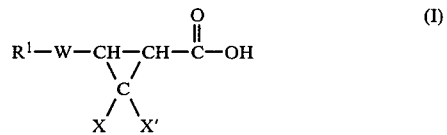

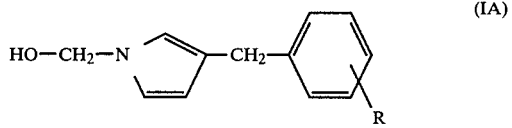

The alcohols of formula IA can be made as described by Ohsumi et al., Offenlegungsschrift No. 28 43 760. The acids of formula I can be made as described in my copending application Ser. No. 942,509, filed Sept. 15, 1978.

The following terms, wherever used in the description herein and the appended claims, have the meaning defined below, unless otherwise specified hereinafter.

The term "lower alkyl" refers to an alkyl group, straight or branched, having a chain length of one to six carbon atoms. The term "lower haloalkyl" refers to an alkyl group substituted with one to three halogen atoms such as chloromethyl, fluoromethyl, trifluoromethyl, 2,2,2-trifluoroethyl, 6-chlorohexyl, 2-fluoroethyl, and the like. The term "lower alkoxy" refers to an alkoxy group, straight or branched, having a chain length of one to six carbon atoms. The term "lower alkylthio" refers to an alkylthio group, straight or branched, having a chain length of one to six carbon atoms.

The term "lower alkenyl" refers to an ethylenically unsaturated hydrocarbon group, straight or branched, having a chain length of two to six carbon atoms and one ro two ethylenic bonds such as vinyl, allyl, 3-butenyl, 2-hexenyl, i-propenyl, 2,4-hexadienyl, and the like. The term "lower haloalkenyl" refers to a lower alkenyl group substituted with one to three halogen atoms.

The term "cycloalkyl" refers to a cycloalkyl group of three to six cyclic carbon atoms.

The term "halogen" refers to bromo, chloro, fluoro or iodo.

The term "lower haloalkoxy" refers to a lower alkoxy group substituted with one to three halogen atoms.

The term "lower acyloxy" refers to a lower organic acyloxy group of one to six carbon atoms, such as acetoxy.

The compounds of the present invention of formula (A) have one or more asymmetric carbon atoms. The present invention includes each of the optical isomers and racemic mixtures thereof. In the examples hereinafter, unless otherwise specified, the compound prepared is a racemic mixture.

The compounds of the present invention of formula (A) ar useful pest control agents, particularly for the control of insects and acarids. In the use of the compounds of formula (A) for combatting insects and acarids for the protection of agricultural crops, for example soybeans, cotton, alfalfa, etc., a compound of formula (A), or mixtures thereof, together with a carrier is applied to the locus in a pesticidally effective amount. The carrier can be liquid or solid and include adjuvants such as wetting agents, dispersing agents and other surface active ingredients. The compounds of formula (A) can be used in formulations such as wettable powders, solutions, dusts, granules, emulsifiable concentrates, and the like. Suitable solid carriers include natural and synthetic silicates and clays, carbon or charcoal granules, natural and synthetic resins, waxes, and the like. Suitable liquid carriers include water, aromatic hydrocarbons, alcohols, vegetable and mineral oils, ketones, and the like. The amount of a compound of formula (A) in the formulation can vary widely, generally within the range of about 0.01 percent to about 90.0 percent, by weight, more usually 0.01 to 25.0 percent.

The compounds of the present invention can be used in combination with other pesticides such as the carbamates, phosphates and insect growth regulators, e.g., propoxur, carbaryl, naled, dichlorvos, phosmet, chlorpyrifos, acephate, diazinon, methoprene, kinoprene, hydroprene, cyhexatin, resmethrin, permethrin and fenvalerate.

The following examples are provided to illustrate the practice of the present invention. Temperature is given in degrees Centigrade. RT means room temperature.

EXAMPLE 1

A mixture of 3-(4-chlorophenoxy)-2,2-dimethylcyclopropanecarboxylic acid (0.95 g, 3.95 mmol), thionyl chloride (0.342 ml, 4.74 mmol) and DMF (several drops) in 50 ml benzene is stirred at RT for 2 days. The solvent and excess thionyl chloride are evaporated under reduced pressure. The resulting acid chloride is dissolved in 50 ml benzene, and 3-benzylpyrrolylmethyl alcohol (3.95 mmol) and 0.482 g 4-dimethtylaminopyridine (3.95 mmol) are added. The mixture is left at 25° for 18 hours and then heated under reflux for 2 hours. The mixture is then poured into water and extracted with ether. The organic phase is washed with dilute HCl, sat. $NaHCO_3$, water and brine, dried and concentrated under vacuum. The crude product is purified by preparative TLC developing with 20% ethyl acetate/hexane to yield 3-benzylpyrrolylmethyl 3-(4-chlorophenoxy)-2,2-dimethylcyclopropanecarboxylate (A; R is hydrogen, X=X' is methyl, W is oxygen, $R^1$ is 4-chlorophenyl).

EXAMPLE 2

3-(4-Fluorophenoxy)-2,2-dimethylcyclopropanecarboxylic acid (3.40 mmol) is stirred together with 0.34 g (3.40 mmol) potassium bicarbonate in 10 ml THF/DMF (1:1) for 15 minutes. Then 3.40 mmol of 3-benzylpyrrolylmethyl methanesulfonate in 5 ml THF/DMF (1:1) is added and the mixture stirred for approximately 48 hours. The reaction is diluted with ether, washed with water (3X) and sat. NaCl, dried and solvent is removed. The crude product is purified by preparative TLC developing with 10% ethyl acetate/hexane to yield 3-benzylpyrrolylmethyl 3-(4-fluorophenoxy)-2,2-dimethylcyclopropanecarboxylate.

EXAMPLE 3

To 10 ml DMF is added 0.88 g 3-(2,2,2-trifluoroethoxy)-2,2-dimethylcyclopropanecarboxylic acid (4.14 mmol) and 1.146 g potassium carbonate (8.29 mmol), after which is added 4.00 mmol of 3-benzylpyrrolylmethyl bromide. This mixture is stirred under nitrogen for 15 hours. The reaction mixture is extracted with ether and the ether phase is washed with water (3X) and brine, and dried over sodium sulfate. The solvent is then removed to yield 3-benzylpyrrolylmethyl 3-(2,2,2-trifluoroethoxy)-2,2-dimethylcyclopropanecarboxylate.

EXAMPLE 4

Each of 3-(4-t-butylphenoxy)-2,2-dimethylcyclopropanecarboxylic acid and 3-(4-methylphenoxy)-2,2-dimethylcyclopropanecarboxylic acid is reacted with thionyl chloride and then with 3-benzylpyrrolylmethyl alcohol to yield, respectively, 3-benzylpyrrolylmethyl 3-(4-t-butylphenoxy)-2,2-dimethylcyclopropanecarboxylate and 3-benzylpyrrolylmethyl 3-(4-methylphenoxy)-2,2-dimethylcyclopropanecarboxylate.

EXAMPLE 5

Each of the carboxylic acids listed under column I is reacted with 3-benzylpyrrolylmethyl alcohol using the procedure of Example 1 or 2 to yield the respective ester under column II.

I 3-(4-chloro-2-fluorophenoxy)-2,2-dimethylcyclopropanecarboxylic acid
3-(2-trifluoromethylphenoxy)-2,2-dimethylcyclopropanecarboxylic acid
3-(4-trifluoromethylphenoxy)-2,2-dimethylcyclopropanecarboxylic acid
3-(2-fluorophenoxy)-2,2-dimethylcyclopropanecarboxylic acid
3-(2,4-difluorophenoxy)-2,2-dimethylcyclopropanecarboxylic acid
3-(2-chlorophenoxy)-2,2-dimethylcyclopropanecarboxylic acid
3-(2-methylphenoxy)-2,2-dimethylcyclopropanecarboxylic acid
3-(2-chloro-4-methylphenoxy)-2,2-dimethylcyclopropanecarboxylic acid
3-(4-chloro-2-nitrophenoxy)-2,2-dimethylcyclopropanecarboxylic acid
3-(2-fluoro-4-trifluoromethylphenoxy)-2,2-dimethylcyclopropanecarboxylic acid
3-(4-bromo-2-chlorophenoxy)-2,2-dimethylcyclopropanecarboxylic acid

II 3-benzylpyrrolylmethyl 3-(4-chloro-2-fluorophenoxy)-2,2-dimethylcyclopropanecarboxylate
3-benzylpyrrolylmethyl 3-(2-trifluoromethylphenoxy)-2,2-dimethylcyclopropanecarboxylate
3-benzylpyrrolylmethyl 3-(4-trifluoromethylphenoxy)2,2-dimethylcyclopropanecarboxylate
3-benzylpyrrolylmethyl 3-(2-fluorophenoxy)-2,2-dimethylcyclopropanecarboxylate
3-benzylpyrrolylmethyl 3-(2,4-difluorophenoxy)-2,2-dimethylcyclopropanecarboxylate
3-benzylpyrrolylmethyl 3-(2-chlorophenoxy)-2,2-dimethylcyclopropanecarboxylate
3-benzylpyrrolylmethyl 3-(2-methylphenoxy)-2,2-dimethylcyclopropanecarboxylate
3-benzylpyrrolylmethyl 3-(2-chloro-4-methylphenoxy)-2,2-dimethylcyclopropanecarboxylate
3-benzylpyrrolylmethyl 3-(4-chloro-2-nitrophenoxy)-2,2-dimethylcyclopropanecarboxylate
3-benzylpyrrolylmethyl 3-(2-fluoro-4-trifluoromethylphenoxy)-2,2-dimethylcyclopropanecarboxylate
3-benzylpyrrolylmethyl 3-(4-bromo-2-chlorophenoxy)-2,2-dimethylcyclopropanecarboxylate

EXAMPLE 6

Following the procedure of Example 2, 3-(4-methylphenoxy)-2,2-dimethylcyclopropanecarboxylic acid is reacted with 3-(3-fluorobenzyl)-pyrrolylmethyl methanesulfonate to yield 3-(3-fluorobenzyl)-pyrrolylmethyl 3-(4-methylphenoxy)-2,2-dimethylcyclopropanecarboxylate.

EXAMPLE 7

To a mixture of 3-(4-chlorophenoxy)-2,2-dimethylcyclopropanecarboxylic acid (2.77 mmol), potassium carbonate (3.25 mmol) and hexamethylphosphoric triamide (HMPT) (3 ml), with stirring and under nitrogen, at RT, is added 3-(3-methylbenzyl)-pyrrolylmethyl bromide (2.77 mmol) in THF. The reaction is stirred at RT for about 48 hours and then worked up by partition between water/ether. The organic phase is washed with water and brine, dried over potassium carbonate, filtered and the solvent is removed from the filtrate. The residue is plated on preparatory TLC plates developing with 10% ether/hexane to yield 3-(3-methylbenzyl)-pyrrolylmethyl 3-(4-chlorophenoxy)-2,2-dimethylcyclopropanecarboxylate.

EXAMPLE 8

Following the method of Example 1 or 2, each of the acids of column III

III 3-n-propoxy-2,2-dimethylcyclopropanecarboxylic acid
3-but-2-enoxy-2,2-dimethylcyclopropanecarboxylic acid
3-(3-fluoropropenoxy)-2,2-dimethylcyclopropanecarboxylic acid
3-(t-butoxy)-2,2-dimethylcyclopropanecarboxylic acid
3-(4-chloro-3-fluorobut-2-enoxy)-2,2-dimethylcyclopropanecarboxylic acid is reacted with 3-benzylpyrrolylmethyl alcohol to yield the 3-benzylpyrrolylmethyl ester (column IV).

IV 3-benzylpyrrolylmethyl 3-n-propoxy-2,2-dimethylcyclopropanecarboxylate
3-benzylpyrrolylmethyl 3-but-2-enoxy-2,2-dimethylcyclopropanecarboxylate
3-benzylpyrrolylmethyl 3-(3-fluoropropenoxy)-2,2-dimethylcyclopropanecarboxylate
3-benzylpyrrolylmethyl 3-(t-butoxy)-2,2-dimethylcyclopropanecarboxylate
3-benzylpyrrolylmethyl 3-(4-chloro-3-fluorobut-2-enoxy)-2,2-dimethylcyclopropanecarboxylate

EXAMPLE 9

Following the procedure of Example 1, 3-(4-fluorophenoxy)-2,2-dimethylcyclopropanecarboxylic acid is reacted with each of 3-(4-chlorobenzyl)-pyrrolylmethyl alcohol, 3-(4-methylbenzyl)-pyrrolylmethyl alcohol, and 3-(4-fluorobenzyl)-pyrrolylmethyl alcohol to yield, respectively, 3-(4-chlorobenzyl)-pyrrolylmethyl 3-(4-fluorophenoxy)-2,2-dimethylcyclopropanecarboxylate, 3-(4-methylbenzyl)-pyrrolylmethyl 3-(4-fluorophenoxy)-2,2-dimethylcyclopropanecarboxylate, and 3-(4-fluorobenzyl)-pyrrolylmethyl 3-(4-fluorophenoxy)-2,2-dimethylcyclopropanecarboxylate.

In the same manner, 3-(4-chlorobenzyl)-pyrrolylmethyl 3-(n-butoxy)-2,2-dimethylcyclopropanecarboxylate is produced from 3-(n-butoxy)-2,2-dimethylcyclopropanecarboxylic acid and 3-(4-chlorobenzyl)-pyrrolylmethyl alcohol.

Using the method of Example 1, 3-phenylthio-2,2-dimethylcyclopropanecarboxylic acid is reacted with 3-benzylpyrrolylmethyl alcohol to yield 3-benzylpyrrolylmethyl 3-phenylthio-2,2-dimethylcyclopropanecarboxylate.

The carboxylic acid 3-phenoxy-2,2-dichlorocyclopropanecarboxylic acid is reacted with each of 3-benzylpyrrolylmethyl alcohol and 3-(4-chlorobenzyl)-pyrrolylmethyl alcohol to yield, respectively, 3-benzylpyrrolylmethyl 3-phenoxy-2,2-dichlorocyclopropanecarboxylate and 3-(4-chlorobenzyl)-pyrrolylmethyl 3-phenoxy-2,2-dichlorocyclopropanecarboxylate.

EXAMPLE 10

Following the procedure of Example 1, each of 3-benzylpyrrolylmethyl alcohol, 3-(4-chlorobenzyl)-pyrrolylmethyl alcohol, 3-(4-methylbenzyl)-pyrrolylmethyl alcohol and 3-(4-fluorobenzyl)-pyrrolylmethyl alcohol is reacted with 3-(n-pentyloxy)-2,2-dimethylcyclopropanecarboxylic acid to yield:
3-benzylpyrrolylmethyl 3-(n-pentyloxy)-2,2-dimethylcyclopropanecarboxylate,
3-(4-chlorobenzyl)-pyrrolylmethyl 3-(n-pentyloxy)-2,2-dimethylcyclopropanecarboxylate,
3-(4-methylbenzyl)-pyrrolylmethyl 3-(n-pentyloxy)-2,2-dimethylcyclopropanecarboxylate, and
3-(4-fluorobenzyl)-pyrrolylmethyl 3-(n-pentyloxy)-2,2-dimethylcyclopropanecarboxylate.

EXAMPLE 11

Using the procedure of Example 1, each of the acids
3-(n-propoxy)-2,2-dimethylcyclopropanecarboxylic acid,
3-(n-butoxy)-2,2-dimethylcyclopropanecarboxylic acid, and
3-(n-hexyloxy)-2,2-dimethylcyclopropanecarboxylic acid is reacted with 3-(4-chlorobenzyl)-pyrrolylmethyl alcohol to yield:
3-(4-chlorobenzyl)-pyrrolylmethyl 3-(n-propoxy)-2,2-dimethylcyclopropanecarboxylate,
3-(4-chlorobenzyl)-pyrrolylmethyl 3-(n-butoxy)-2,2-dimethylcyclopropanecarboxylate, and
3-(4-chlorobenzyl)-pyrrolylmethyl 3-(n-hexyloxy)-2,2-dimethylcyclopropanecarboxylate.

EXAMPLE 12

To a stirred solution of 3-benzylpyrrolylmethyl alcohol (1.8 mmol), 3-(n-pentyloxy)-2,2-dimethylcyclopropanecarboxylic acid (2.0 mmol) and 4-dimethylaminopyridine (0.65 mmol) in 20 ml of methylene chloride and 2 ml of DMF is added N,N'-dicyclohexylcarbodiimide (2 mmol). The reaction mixture is stirred, under nitrogen, for about two hours and then filtered and extracted with water. The aqueous phase is extracted with ether. The combined organic phases are washed with saturated aqueous sodium bicarbonate, water and saturated aqueous sodium chloride, dried over calcium sulfate and solvent evaporated. The crude product is chromatographed on a rotary chromatograph eluting with ether/hexane to yield 3-benzylpyrrolylmethyl 3-(n-pentyloxy)-2,2-dimethylcyclopropanecarboxylate.

Using the above procedure, 3-(4-chlorobenzyl)-pyrrolylmethyl alcohol is reacted with 3-(i-butoxy)-2,2-dimethylcyclopropanecarboxylic acid to yield 3-(4- chlorobenzyl)-pyrrolylmethyl 3-(i-butoxy)-2,2-dimethylcyclopropanecarboxylate.

What is claimed is:

1. A compound of the formula (A):

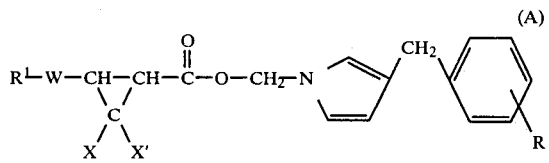

wherein,

W is oxygen or sulfur;

X is lower alkyl or halogen;

X' is hydrogen, lower alkyl or halogen;

$R^1$ is lower alkyl, lower haloalkyl, lower alkenyl, lower haloalkenyl, or the group

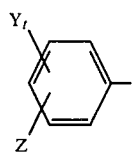

in which t is zero, one, two, three or four;

Y is independently selected from hydrogen, lower alkyl, lower haloalkyl, lower alkoxy, lower alkylthio, lower alkylcarbonyl, lower alkoxycarbonyl, lower acyloxy, halogen, cyano, nitro and lower haloalkylthio;

Z is independently selected from the values of Y, cycloalkyl and lower haloalkoxy; or together with Y forms a methylenedioxy group; and R is hydrogen, fluoro, bromo, chloro, trifluoromethyl, methyl, methoxy or methylthio.

2. A compound according to claim 1 of the formula:

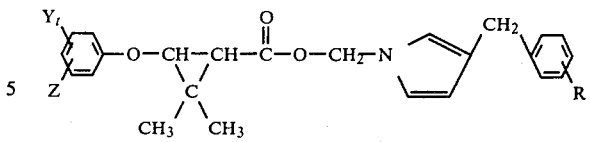

3. A compound according to claim 2 wherein t is zero and Z is in the para position.

4. A compound according to claim 3 wherein Z is hydrogen, chloro, fluoro, bromo, trifluoromethyl, lower alkyl of 1 to 4 carbon atoms, lower alkoxy of 1 or 2 carbon atoms or lower alkylthio of 1 or 2 carbon atoms.

5. A compound according to claim 4 wherein R is hydrogen.

6. A compound according to claim 4 wherein R is fluoro and R is in the para or meta position.

7. A compound according to claim 1 wherein $R^1$ is lower alkyl and each of X and X' is methyl.

8. A compound according to claim 7 wherein $R^1$ is lower alkyl of 3 to 6 carbon atoms.

9. A compound according to claim 8 wherein R is hydrogen or fluoro.

10. A compound according to claim 9 wherein R is hydrogen.

11. A compound according to claim 8 wherein $R^1$ is a primary or secondary lower alkyl group of 3 to 6 carbon atoms.

12. A compound according to claim 11 wherein R is hydrogen.

13. A compound according to claim 11 wherein R is fluoro and R is in the meta or para position.

14. A compound according to claim 13 wherein R is in the para position.

15. The compound, 3-benzylpyrrolylmethyl 3-(n-pentyloxy)-2,2-dimethylcyclopropanecarboxylate, according to claim 12.

16. The compound, 3-benzylpyrrolylmethyl 3-(n-propoxy)-2,2-dimethylcyclopropanecarboxylate, according to claim 12.

17. The compound, 3-(4-fluorobenzyl)-pyrrolylmethyl 3-(n-pentyloxy)-2,2-dimethylcyclopropanecarboxylate, according to claim 14.

* * * * *